(12) United States Patent
Dragan

(10) Patent No.: US 9,301,915 B2
(45) Date of Patent: Apr. 5, 2016

(54) PROTECTIVE WAX FOR BLEACHED TEETH

(71) Applicant: Centrix, Inc., Shelton, CT (US)

(72) Inventor: William B. Dragan, Easton, CT (US)

(73) Assignee: Centrix, Inc., Shelton, CT (US)

( * ) Notice: Subject to any disclaimer, the term of this patent is extended or adjusted under 35 U.S.C. 154(b) by 0 days.

(21) Appl. No.: 14/552,936

(22) Filed: Nov. 25, 2014

(65) Prior Publication Data
US 2015/0079010 A1    Mar. 19, 2015

Related U.S. Application Data

(63) Continuation of application No. PCT/US2013/043504, filed on May 31, 2013.

(60) Provisional application No. 61/654,578, filed on Jun. 1, 2012.

(51) Int. Cl.
*A61K 8/67* (2006.01)
*A61K 8/92* (2006.01)
*A61K 8/24* (2006.01)
*A61Q 11/00* (2006.01)
*A61K 8/31* (2006.01)
*A61K 8/02* (2006.01)

(52) U.S. Cl.
CPC .............. *A61K 8/92* (2013.01); *A61K 8/0216* (2013.01); *A61K 8/24* (2013.01); *A61K 8/31* (2013.01); *A61K 8/678* (2013.01); *A61Q 11/00* (2013.01); *A61K 2800/884* (2013.01)

(58) Field of Classification Search
USPC .................................. 424/49, 52, 53; 433/215
See application file for complete search history.

(56) References Cited

U.S. PATENT DOCUMENTS

| 5,037,639 | A | 8/1991 | Tung | 424/57 |
| 5,268,167 | A | 12/1993 | Tung | 424/52 |
| 5,437,857 | A | 8/1995 | Tung | 424/52 |
| 5,665,333 | A | 9/1997 | Homola et al. | 424/54 |
| 6,652,875 | B1 | 11/2003 | Bannister | 424/440 |
| 2002/0064541 | A1 | 5/2002 | Lapidot et al. | 424/401 |
| 2003/0206939 | A1 | 11/2003 | Bannister | 424/440 |
| 2005/0249677 | A1 | 11/2005 | Malcamcher et al. | 424/53 |
| 2006/0099155 | A1 | 5/2006 | MacDonald et al. | 424/53 |
| 2009/0181071 | A1 | 7/2009 | St. John et al. | 424/443 |
| 2010/0040565 | A1 | 2/2010 | Homola et al. | 424/49 |
| 2011/0104219 | A1 | 5/2011 | Rajaiah et al. | 424/401 |

FOREIGN PATENT DOCUMENTS

WO    WO2011133793    * 10/2011    ............ G06F 15/177

OTHER PUBLICATIONS

Supplementary European Search report dated Oct. 12, 2015 in corresponding EPO Application No. EP 13 79 7373.

* cited by examiner

*Primary Examiner* — Walter Webb
(74) *Attorney, Agent, or Firm* — Fattibene and Fattibene LLC; Paul A. Fattibene

(57) ABSTRACT

A protective coating material applied to whitened or bleached teeth. The protective coating material comprises microcrystalline wax, mineral oil, vitamin E, and amorphous calcium phosphate or ACP. The protective coating material covers the whitened or bleached tooth surface protecting it from staining thereby prolonging the whiteness of the teeth. The whitened or bleached damaged tooth enamel may also be strengthened or repaired.

4 Claims, 5 Drawing Sheets

PROTECTIVE WAX FOR BLEACHED TEETH

RELATED APPLICATIONS

This application is a continuation of International Application PCT/US2013/043504, with an international filing date of May 31, 2013, which claims the benefit of U.S. Provisional Application No. 61/654,578 filed Jun. 1, 2012, all of which are herein incorporated by reference.

FIELD OF THE INVENTION

The present invention relates in general to protecting and repairing teeth that have been bleached, and particularly to a protective wax coating that maintains, protects, repairs, and preserves bleached teeth prolonging their white appearance.

BACKGROUND OF THE INVENTION

The public today is concerned about their appearance, youth, and especially about their smile. There is much that has been accomplished in dentistry today that enhances the ability of the teeth to become white as the teeth once were in the persons youth. This can be accomplished by the use of crowns, veneers and bleaching. As a result, cosmetic dentistry has become very popular. Many people would like to have whiter and brighter teeth. As a result whitening or bleaching of teeth has become very common. However, all these means require a substantial investment on the part of the person.

The maintenance of the crowns and veneers, once they have been restored with porcelain, is slight because of the sealed surface of the porcelain. This is not true of natural teeth that have been whitened or bleached. The surface of bleached teeth reveals a surface that is full of cracks and crevices that is the result of the bleaching process. Therefore, these damaged surfaces are able to easily pickup pigments that are in our food and habits. Some of these pigments or staining products are; red wine, coffee, tea, lipstick, nicotine from smoking, food with any color. All these things have a tendency to stain and color the teeth that have been bleached. The solution to this is to re-bleach these teeth. The problem is that this will cause further damage to the previously bleached enamel and continual bleaching may lead to serious damage to the teeth and even result in the need for a root canal in order to save them.

Generally, the tooth bleaching process uses a form of hydrogen peroxide which whitens, and oxidizes the enamel of the tooth opening the enamel permitting it to be easily stained. In order to maintain their whiteness teeth must be periodically bleached. Repeated bleaching may potentially damage the enamel of the teeth. Often this damage creates pits and fissures in the enamel resulting in porosity that results in the teeth being more easily stained and discolored.

There have been coatings placed on teeth in an effort to provide a bacteria inhibiting film. One such protective coating is disclosed in U.S. Pat. No. 5,665,333 entitled "Methods, Compositions, and Dental Delivery Systems for the Protection of the Surface of Teeth", issuing to Homola et al. on Sep. 9, 1997, which is herein incorporated by reference. Therein disclosed is a protective coating particularly adapted to provide a bacteria inhibiting film on the surface of a tooth. A transfer agent and barrier material is used to improve the adhesion of the protective coating on the surface of the tooth.

Other coatings or materials have also been applied to teeth. One such material is amorphous calcium phosphate or ACP which has been applied to teeth to remineralize the teeth. The use of a ACP to remineralize teeth is disclosed in U.S. Pat. No. 5,037,639 entitled "Methods and Compositions for Mineralizing Calcified Tissues" issuing to Tongue on Aug. 6, 1991, which is herein incorporated by reference. Therein disclosed is a method of applying a composition containing amorphous calcium phosphate or ACP to teeth to remineralize the teeth.

While the prior protective coatings are well adapted to provide a bacteria inhibiting film or remineralizing of teeth, they are not necessarily suitable for use in maintaining whiter teeth and protecting whitened teeth. Therefore, there is a need to provide a protective coating specifically adapted for maintaining the whiteness of teeth and protecting them from damage when they have been bleached.

SUMMARY OF THE INVENTION

The present invention is a protective coating applied to teeth that have been whitened that maintains their whiteness and helps to repair damage caused by the whitening or bleaching of the teeth. A microcrystalline wax is mixed with vitamin E, mineral oil, and amorphous calcium phosphate providing a smooth consistent wax material that may be easily applied to whitened teeth. The protective coating prevents staining and the amorphous calcium phosphate helps to repair the damaged tooth surface caused by the repeated whitening of the teeth.

Accordingly it is an object of the present invention to maintain the color of whitened teeth.

It is another object of the present invention to extend the time between teeth whitening procedures.

It is yet another object of the present invention to protect teeth and repair damage to teeth that have been whitened.

It is an advantage of the present invention that it reduces the need to repeatedly whiten teeth.

It is another advantage of the present invention that it is easy to apply to the teeth.

Is a feature of the present invention that it has a creamy consistency and is easy to apply.

It is another feature of the present invention that it contains amorphous calcium phosphate.

These and other objects, advantages, and features will become more readily apparent in view of the following more detailed description.

DETAILED DESCRIPTION OF THE PREFERRED EMBODIMENTS

Figure 1:
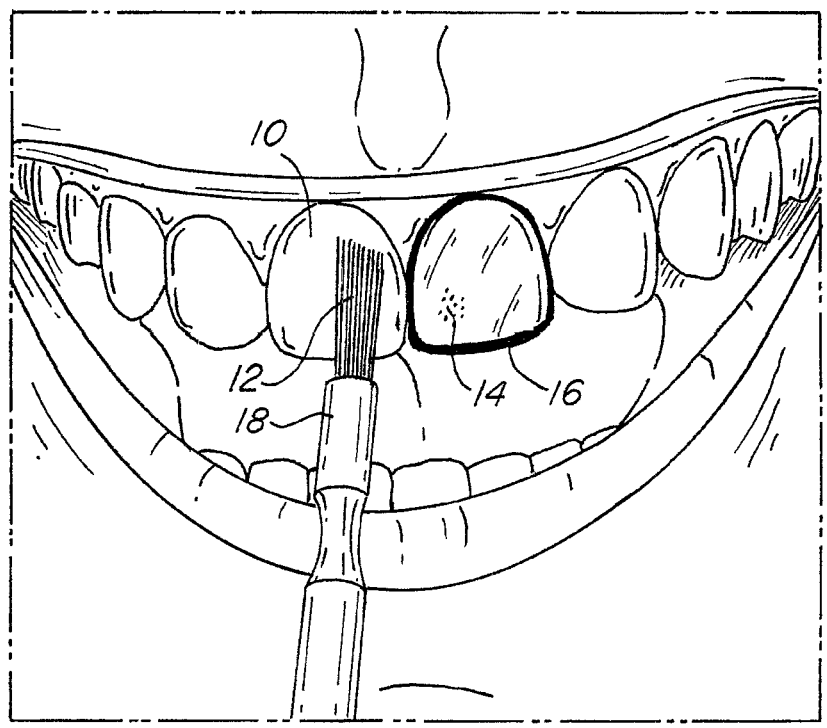
FIG. 1 schematically illustrates the present invention applied to a tooth surface.

The present invention is a protective coating material specifically adapted for maintaining and protecting bleached teeth so as to seal and prevent teeth from being exposed to stains. The protective coating material of the present invention is easy to apply and adheres to the teeth for a prolonged period of time. The present invention also may help to strengthen tooth enamel and possibly reverse the damage caused by bleaching. The present invention uses a mixture of microcrystalline wax, oils, such as vitamin E and mineral oil, amorphous calcium phosphate, and aromatic or flavoring oils such as peppermint. Amorphous calcium phosphate is a material that has been shown to repair damaged tooth enamel. The microcrystalline wax has fine crystals and is tackier and more elastic than paraffin waxes. Therefore, the microcrystalline wax is particularly well-suited for applying to teeth.

A preferred formulation that has proven to work particularly well on bleached teeth is described below.

The process of making the protective coating material consisted of heating and melting 30 grams of microcrystalline wax to a temperature of 180° C. Once the microcrystalline wax was melted, 12 mL of vitamin E were mixed until the mixture was water clear. 40 mL of mineral oil was added to the melted wax and mixed until water clear. The wax mixture was taken off the heat and 1 gram of amorphous calcium phosphate dissolved in 2 to 4 mL of acetone was added. The solution of amorphous calcium phosphate was poured into the wax mixture and stirred until the mixture was uniformly white in color and the wax mixture began to solidify. The wax mixture was then cooled and solidified to a creamy consistency.

In another procedure or method of making the protective coating material, the amorphous calcium phosphate, rather than being dissolved in the acetone, may be dissolved in the mineral oil. This eliminates the need for the acetone.

After cooling the protective coating material is applied in a thin coat to the bleached teeth. The protective coating material can be applied by any means, such as a brush, Q-tip, or any other applicator to evenly distribute the protective coating material to the bleached teeth. The protective coating material may also be applied by a finger or lipstick-like container. The protective coating material may be applied once every two to three days to protect the teeth and prevent the teeth from staining so as to maintain their whiteness.

The table below indicates the desired formulation for a protective coating material that has proven to work especially well in protecting and maintaining teeth white after whitening or bleaching.

| PERCENT BY WEIGHT | MATERIAL |
| --- | --- |
| 35 to 45%, preferably substantially 39% | Microcrystalline wax |
| 10 to 20%, preferably substantially 15% | Vitamin E |
| 40 to 50%, preferably substantially 45% | Mineral Oil |
| 0.5 to 1.5%, preferably substantially 1% | Amorphous Calcium Phosphate (ACP) |
| .0005 to .001%, preferably a trace amount | Flavoring |

The formulation indicated in the above table has proven to result in a desirable consistency and color or transparency of the protective coating material. However, it should be appreciated that the formulation may be modified as desired to provide a desired consistency or texture for a particular circumstance or application. Accordingly, if the oil content is reduced the viscosity and hardness will increase and may make the protective coating material more difficult to apply. If the amorphous calcium phosphate, ACP, is increased an opaque protective coating material may result changing the color of the teeth. If the oil content is increased the protective coating material may become runny and unmanageable.

The protective coating material of the present invention greatly facilitates the maintaining of white teeth and prevents the need for frequent repeated bleaching, which may damage the teeth.

Studies have been performed in which the protective coating material of the invention has prevented teeth from staining. The protective coating material of the present invention is safe and can be easily applied by an individual. The protective coating material of the invention may be sold in a kit together with or without a tooth whitening or bleaching material.

FIG. 1 illustrates the protective coating material applied to a tooth. In FIG. 1 a tooth 10 has a tooth surface 12. The tooth surface 12 often has irregularities or bleach damage 14 caused by bleaching. The irregularities or bleach damage 14 may be comprised of small pits and fissures or simply porosity of the tooth 10 enamel. The protective coating material 16 is illustrated applied to the tooth surface 12 with a brush 18. The protective coating material 16 acts as a barrier to stains adhering to the tooth surface 12. Additionally, the protective coating material 16 greatly assists and facilitates the protection and repair of the bleached damaged tooth enamel.

Figure 2:
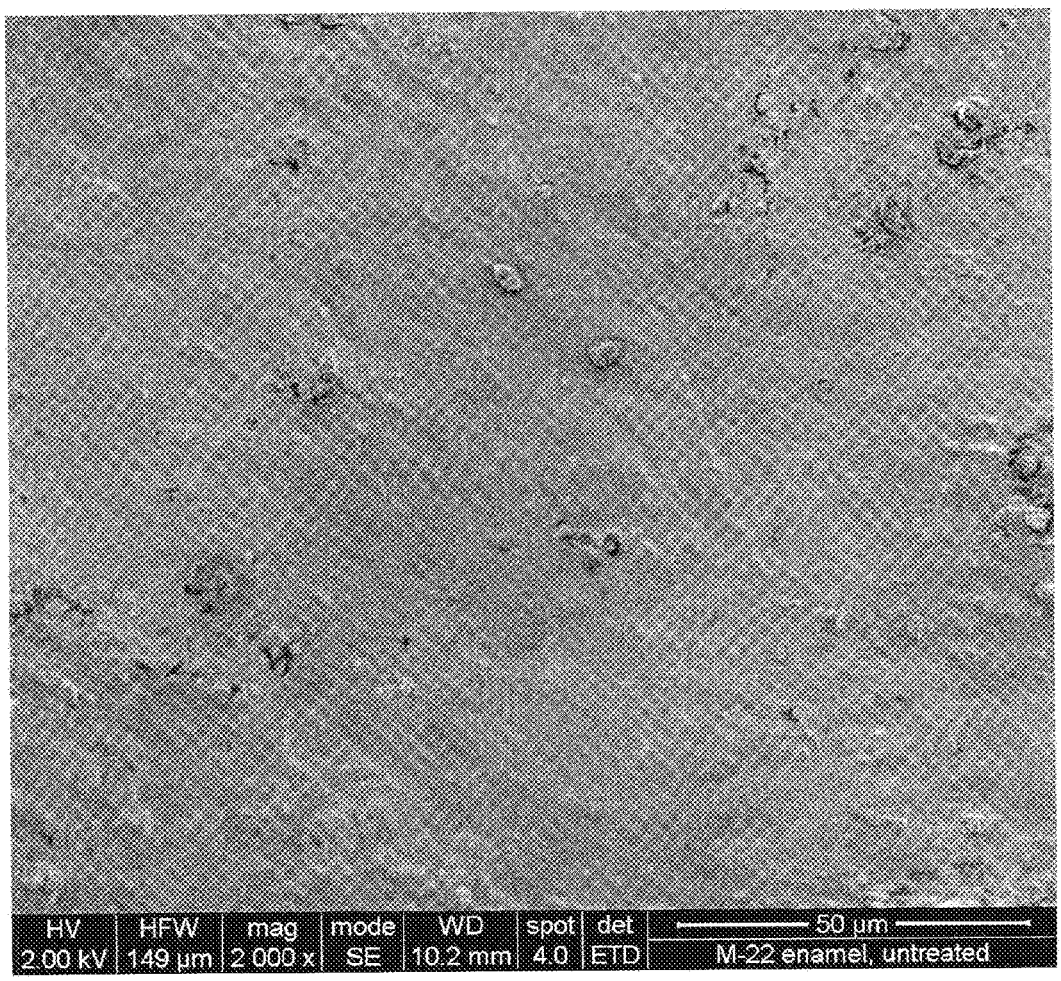
FIG. 2 is a highly magnified image of tooth enamel that has not been bleached.

FIG. 2 is a picture of highly magnified untreated tooth enamel taken with a scanning electron microscope, SEM. As can be seen in FIG. 2, untreated tooth enamel is relatively smooth with a surface resistant to staining or discoloration.

Figure 3:
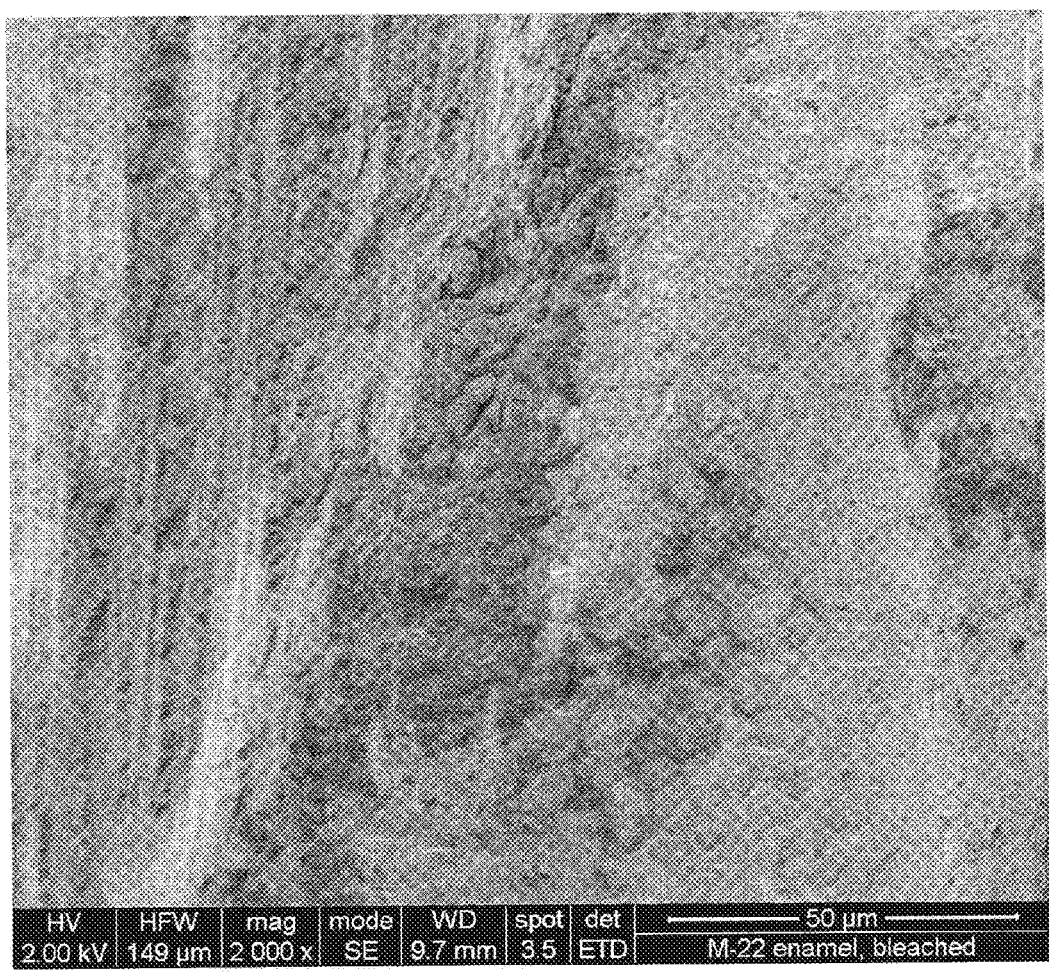
FIG. 3 is a highly magnified image of tooth enamel that has been bleached.

FIG. 3 is a picture of highly magnified whitened or bleached tooth enamel taken with a scanning electron microscope, SEM. As can be seen in FIG. 3, the whitened or bleached tooth enamel is rough and has an irregular surface with the enamel rod ends exposed by the whitening or bleaching of the tooth enamel. In this condition the tooth enamel is very susceptible to staining or discoloration.

Figure 4:
FIG. 4 is a highly magnified image of tooth enamel that has been treated with the protective wax of the present invention.

FIG. 4 is a picture of highly magnified protective coating material of the present invention applied to whitened or bleached tooth enamel taken with a scanning electron microscope, SEM. As can be seen in FIG. 4, the protective coating wax material fills in and covers the rough or irregular surface of the whitened bleached tooth enamel providing a smooth even coating.

Figure 5:
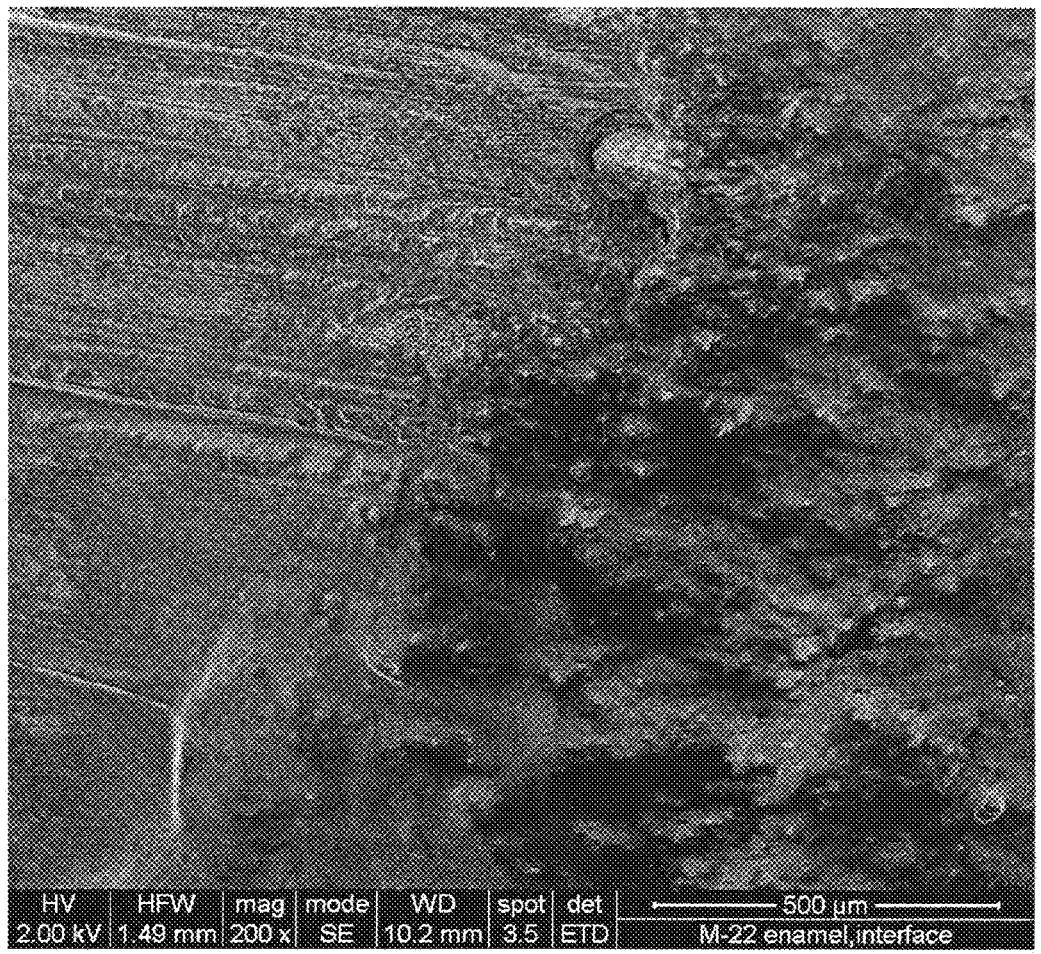
FIG. 5 is a magnified image of tooth enamel that has been partially treated with the protective wax of the present invention.

FIG. 5 is a picture of magnified whitened or bleached tooth enamel, on the left, and the protective coating wax material applied to the whitened or bleached tooth enamel, on the right. The picture in FIG. 5 has a magnification substantially less than the pictures in FIGS. 2-4. The uncoated whitened or bleached tooth enamel on the left has a damaged roughened or uneven surface with the enamel rods showing. The coated whitened or bleached enamel, on the right, illustrates the protective coating material covering the damaged roughened or uneven surface and the exposed enamel rods of the whitened or bleached tooth enamel.

The invention provides a simple relatively easily manufactured protective material coating that is easily and safely applied to whitened teeth so as to prolong their whiteness. The invention is safe and effective and can be applied as often as desired in order to maintain whiter teeth. The invention may also repair damaged tooth enamel to 2 the harsh chemicals used in whitening teeth. The protective material coating may also be provided together with a whitening agent in a single package or kit as a convenience to the user.

While the preferred embodiments and methods of the present invention have been shown and described herein, it will be apparent to those skilled in the art that various modifications and variations may be made without departing from the spirit and scope of the invention as claimed herein.

What is claimed is:

1. A method of maintaining whiter teeth comprising the steps of:
   applying a whitening material to teeth;
   applying a protective coating material to the teeth after the step of applying the whitening material, wherein the protective coating material comprises, a microcrystalline wax;
vitamin E;
mineral oil; and
amorphous calcium phosphate.

2. A method of maintaining whiter teeth as in claim 1 wherein:
the microcrystalline wax is between 35% and 45% by weight;
the vitamin E is between 10% and 20% by weight;
the mineral oil is between 40% and 45% by weight; and
the amorphous calcium phosphate is between 0.5% and 1.5% by weight.

3. A method of maintaining whiter teeth as in claim 2 wherein:
the microcrystalline wax is 39% by weight;
the vitamin E is 15% by weight;
the mineral oil is 45% by weight; and
the amorphous calcium phosphate is 1% by weight.

4. A method of maintaining whiter teeth as in claim 1 wherein:
the protective coating material further comprises a flavoring.

\* \* \* \* \*